United States Patent
Rutkowski

[11] Patent Number: 6,096,531
[45] Date of Patent: Aug. 1, 2000

[54] METHODS AND COMPOSITIONS FOR BIOREMEDIATION

[75] Inventor: Anthony Alfons Rutkowski, Huntington, Vt.

[73] Assignee: Green Mountain Laboratories, Inc., Montpelier, Vt.

[21] Appl. No.: 09/145,788

[22] Filed: Sep. 2, 1998

[51] Int. Cl.[7] ..................................................... B09B 3/00
[52] U.S. Cl. ....................................................... 435/262.5
[58] Field of Search .................................. 435/170, 171, 435/262, 262.5

[56] References Cited

U.S. PATENT DOCUMENTS

| | | | |
|---|---|---|---|
| 5,484,729 | 1/1996 | DeWeerd et al. | 435/262.5 |
| 5,932,472 | 8/1999 | Abdullah | 435/262.5 |
| 5,955,350 | 9/1999 | Soni et al. | 435/264 |

*Primary Examiner*—David A. Redding
*Attorney, Agent, or Firm*—Kevin M. Farrell

[57] ABSTRACT

Disclosed are methods for assembling a consortium of specific degraders of a xenobiotic compound of interest. A first population of microorganisms is provided, the first population being isolated from a first source containing the xenobiotic compound of interest. The first population of microorganisms is then incubated under conditions appropriate for growth with media containing the xenobiotic compound of interest as a carbon source. The population of then screened for the ability to initiate degradation of the xenobiotic compound of interest. Accumulating intermediate are identified in the degradation pathway of the xenobiotic compound of interest. A second population of microorganisms is then isolated from a source containing the accumulating intermediate in the xenobiotic degradation pathway, or structural homologs thereof. The second population of microorganisms is then incubated under conditions appropriate for growth with media containing the accumulating intermediate as a carbon source. Screening for the ability of the second population of microorganisms to degrade the accumulating intermediate is then carried out. Optionally, the steps recited above can be repeated to identify additional accumulating intermediates, and populations of microorganisms which specifically degrade such additional accumulating intermediates. The populations identified in this manner are then combined under conditions appropriate for the integration of the populations into a single consortium of specific degraders of the xenobiotic compound of interest. Consortia assembled by these methods can then be employed in connection with methods for degrading a xenobiotic compound of interest.

13 Claims, 3 Drawing Sheets

METHODS AND COMPOSITIONS FOR BIOREMEDIATION

BACKGROUND OF THE INVENTION

The "principle of microbial infallibility" (Alexander, *Advances in Applied Microbiology* 7: 35–80 (1965)) is an expression of the empirical observation that there are no natural organic compounds which are totally resistant to biodegradation provided favorable environmental conditions. The postulate is that biopolymers have evolved over billions of years and parallel evolution of microbes which derive energy from the catabolism of such molecules has kept pace.

However, the last half century has ushered in the explosive development of synthetic organic chemistry which has yielded the large-scale production of a staggering array of synthetic organic compounds. Many of these compounds have been released, either intentionally or by accident, into the environment.

Many synthetic organic compounds are sufficiently similar to natural compounds to be recognized and degraded by microbes. However, there is another class of synthetic organics which possess molecular structures and chemical bond sequences which are not recognized by microbial enzymes. These compounds, as a class, are referred to as xenobiotics. Xenobiotic compounds are either totally resistant to degradation (recalcitrant), or are-metabolized incompletely. Common features of recalcitrant compounds include, for example, unusual substitutions such as chlorine and other halogens, unusual bonds or bond sequences such as tertiary and quaternary carbon atoms, highly condensed aromatic rings, excessive molecular size, etc.

A xenobiotic class which has proven to be particularly damaging to the environment is the polychlorinated biphenyl (PCB) class. These compounds consist of a biphenyl ring structure with varying degrees of chlorine substitution. PCBs exhibit an array of interesting and useful traits which are generally dependent upon their degree of chlorination. Prior to the ban on PCB production in the United States, the compounds were commonly used as insulators, flame retardants and lubricants. Through widespread use, PCBs became essentially ubiquitous in the environment, concentrating primarily in soils and sediments due to their insolubility in water and bioconcentration in the fatty tissue of many animal species. Recognition of their deleterious effects on fragile ecosystems and human health has led to the investigation of methods for the remediation of contaminated matrices. To date, however, the method of choice remains dredging of sediments and soils, followed by incineration, a generally inefficient process resulting in the liberation of dioxins and furans.

Alternative methods have been sought, but thus far, none have proven both efficient and cost effective. In light of the presence of a biphenyl nucleus which may be attacked by a number of organisms, PCBs would appear to be prime candidates for biodegradation. This, however, has not proven to be the case. PCBs have been found to be extremely resistant to biodegradation, a circumstance which has contributed to their longevity in the environment. Among the reasons for this recalcitrance is the high degree of variability in size and charge between individual molecules of a given PCB. Unlike most compounds, PCBs as manufactured are mixtures varying in the number and position of chlorine atoms attached to the biphenyl core, with the average weight % of chlorine serving as the common basis for classifying these substances. Thus, biodegradation of these mixtures would require that the organisms involved possess enzyme systems with an unusually low substrate specificity. Further, the transformation products themselves are toxic to the organisms which produce them. Most notable of these by-products are two compounds which are generated after cleavage of the biphenyl core. These are chlorobenzoates and chlorocatechols. These compounds inhibit dioxygenase, which in turn catalyzes the initial hydroxylation of PCBs. Although both of these groups of compounds have the potential for biodegradation, organisms which exhibit the capacity to do so are notably lacking in PCB contaminated soils.

It may be speculated that it is these two blocks to mineralization, enzyme specificity and generation of toxic transformation products, which lead to two patterns of weathering found in PCB contaminated soils and sediments. One is the utilization of low molecular weight species leading to the apparent accumulation of the high molecular weight congeners. The other opposing possibility is the degradation of all cogeners, with the progressive dechlorination of high molecular weight species leading to an apparent accumulation of lower weight forms. Both of these are self limiting, either as the system runs out of cogeners, which fit the available battery of enzymes, or as toxic intermediate accumulate, opening the feedback "switch."

This situation, in which the genetic material to carry out the entire process is available in separate organisms, would appear to be ideally suited to the talents of the biotechnology industry which, through cloning techniques, could theoretically combine these traits in a single cell. However, the release of manipulated organisms into the environment on a large scale is strictly regulated, negating the potential utility of such an approach.

SUMMARY OF THE INVENTION

The present invention relates, in one aspect, to methods for assembling a consortium of specific degraders of a xenobiotic compound of interest. A first population of microorganisms is provided, the first population being isolated from a first source containing the xenobiotic compound of interest, or structural homologs thereof. The first population of microorganisms is then incubated under conditions appropriate for growth with media containing the xenobiotic compound of interest as a carbon source. The population is then screened for the ability to initiate degradation of the xenobiotic compound of interest. Accumulating intermediate are identified in the degradation pathway of the xenobiotic compound of interest. A second population of microorganisms is then isolated from a source containing the accumulating intermediate in the xenobiotic degradation pathway, or structural homologs thereof. The second population of microorganisms is then incubated under conditions appropriate for growth with media containing the accumulating intermediate as a carbon source. Screening for the ability of the second population of microorganisms to degrade the accumulating intermediate is then carried out. Optionally, the steps recited above can be repeated to identify additional accumulating intermediates, and populations of microorganisms which specifically degrade such additional accumulating intermediates. The populations identified in this manner are then combined under conditions appropriate for the integration of the populations into a single consortium of specific degraders of the xenobiotic compound of interest. Consortia assembled by these methods can then be employed in connection with methods for degrading a xenobiotic compound of interest.

DETAILED DESCRIPTION OF THE INVENTION

Figure 1A:
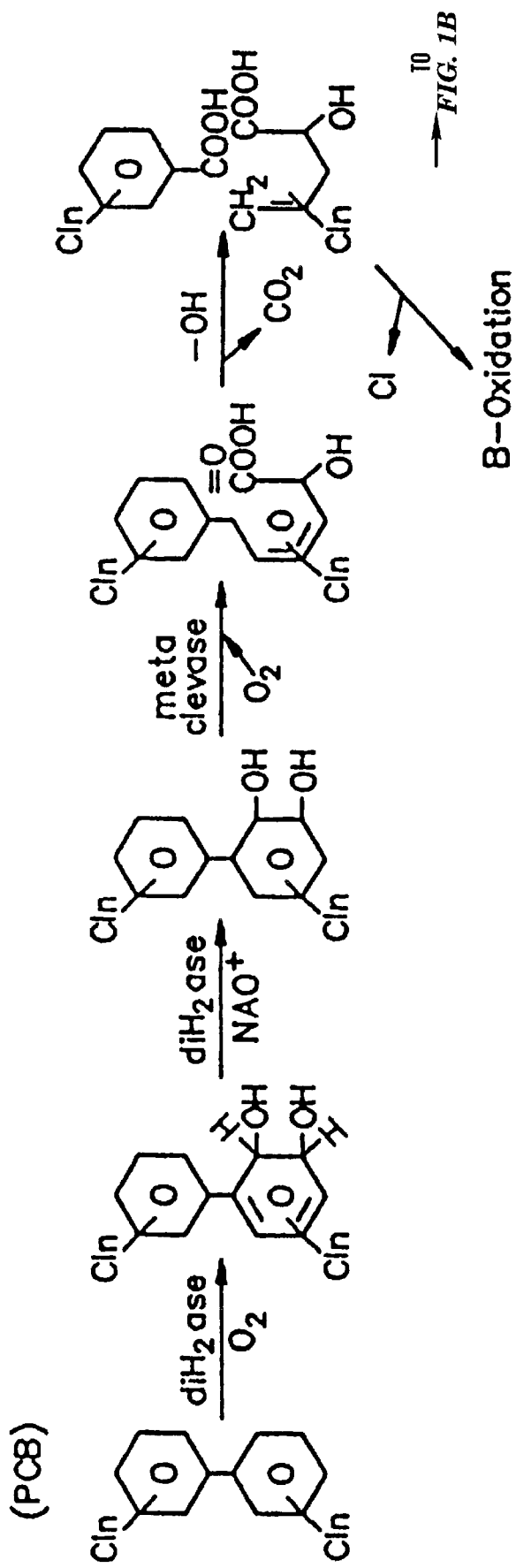
FIG. 1 is a diagrammatic representation of a biochemical pathway for the aerobic biodegradation of PCBs.

The subject invention relates to compositions and methods for the bioremediation of xenobiotic compounds such as PCBs and coal tars. In one aspect, the invention relates to a method for assembling a consortium of specific degraders of such compounds. By way of example, PCBs will be specifically discussed in the following paragraphs. However, it will be recognized by one of skill in the art that the teaching can be applied to the degradation of other xenobiotic compounds through the application of merely routine experimentation.

An initial step in this method is the collection of a first population of microorganisms isolated from a first P(B contaminated matrix. Organisms capable of beginning the transformation of PCBs may be obtained from a variety of sources. Soils, sediments and water which have been contaminated with the target compound may serve as ready made enrichment cultures, if the contaminant is present in sufficient concentration and under such conditions as to enable the support of a population capable of utilizing it. These criteria are not always met, hence secondary sources may be desirable. Selection of a secondary source should include consideration of such parameters as oxygen tension, moisture content and pH, under which the organism(s) being sought will be expected to operate. Further, it should be rich in naturally occurring analogs of the target (e.g., lignins, tannins, resins, etc.).

The first population of microorganisms is initially subjected to a primary enrichment step. It is noted that the enrichments steps described below represent particularly convenient modes of enrichment. However, one of skill in the art will recognize that other enrichment modes consistent with the teachings of this disclosure can be developed through the use of routine experimentation. Primary enrichment is a 2–3 stage process beginning with the depletion of extraneous carbon sources in the sample matrix. This is accomplished, for example, by mixing a portion of the contaminated matrix source. Examples of such mixtures include, for example, a slurry of 20 grams of soil sediment or 20 mL of water sample with 500 mL of mineral salts broth amended with 20 mg/L of Dextrose. This preparation is then monitored for indications of PCB reduction. For example, the preparation can be poured over a base of 500 mL, 2% agar in a large Pyrex dish with a loose fitting lid. When the medium exhibits acidification (an indication of PCB reductive dechlorination), the broth layer is removed to the top of the sediment in the case of soil samples, or to the extent of $\frac{2}{3}$ of its total volume in the case of water samples. This volume is then replaced with a fresh carbon source such as glucose mineral salts broth and the process repeated. Upon acidification and removal of the second broth overlay, a third overlay of mineral salts without glucose can be prepared and added.

At this point, one of two paths may be followed, depending on the water solubility of the target compounds. It should be noted that the use of coverslip cultures offer a convenient method of dealing with either water soluble or water insoluble compounds.

For water insoluble compounds such as PCBs or coal tars, the target compound or its surrogate should be added as a film deposited on the surface of a clean glass coverslip. This is accomplished by preparing a 10 ppm solution of the compound in an appropriate volatile solvent. A series of at least 20 clean coverslips is then inoculated on one side with 20 mL of the solution, and the solvent is then allowed to evaporate. The coverslips are then inserted into the agar base by one corner, deeply enough to remain stable upon prolonged incubation.

Water soluble analytes may be added directly to the mineral salts broth to a final concentration of 10 ppm, unless known microbial toxicity data indicate otherwise. The broth and clean coverslips are added to the agar base as described above. The cultures are placed at 20° C.; alternatively they may be incubated at the average temperature at which they will be expected to perform.

Twenty four hours after implanting the coverslips, the first coverslip is aseptically removed from its agar base, and after light rinsing with sterile buffered water, transferred to a 40 mL VOA vial to which the target analyte has been added in the same fashion as to the coverslips. Each vial should contain, in addition to the target compound, 10 mL of sterile mineral salts broth. At this stage, system appropriate additions may be made in the form of electron doners, vitamins, cofactors, etc.

Figure 1B:
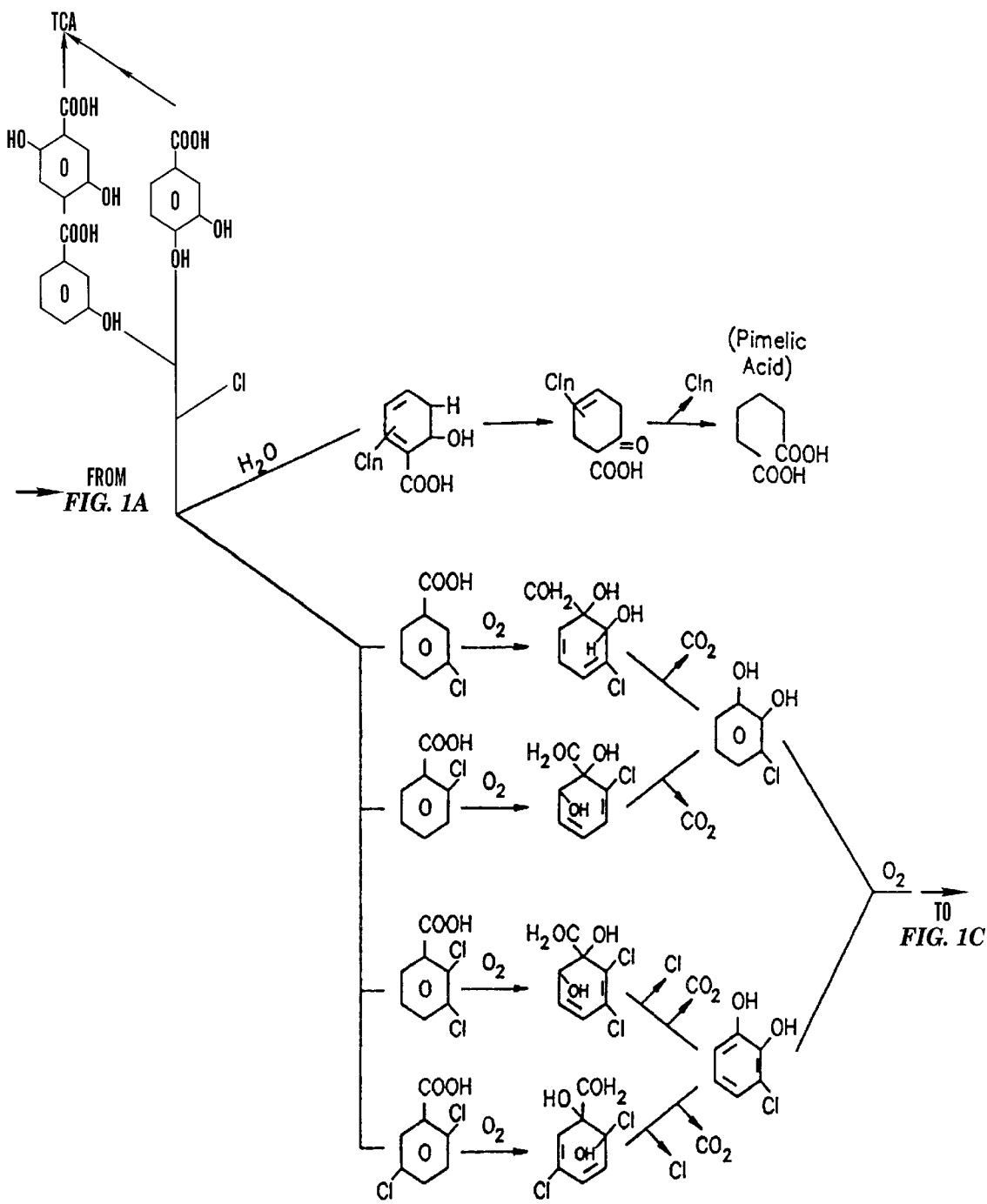
Figure 1C:
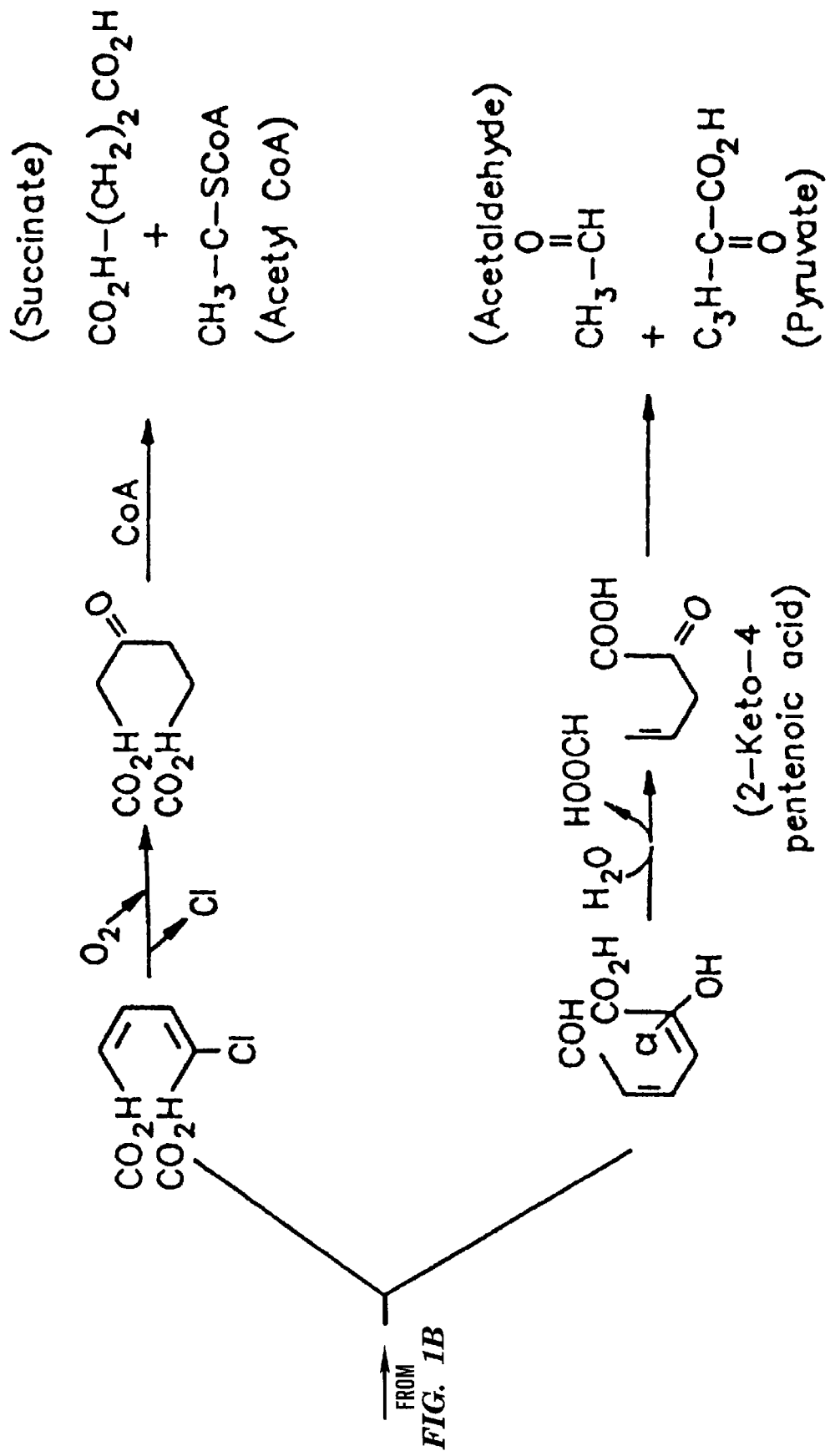

At least one coverslip per day should be removed and treated as described above for a period of 20–30 days. As growth appears in each vial, it is passed to a similar second vial. As each original parent vial reaches an age of approximately two weeks, it is recharged with fresh mineral salts broth and returned to incubation. At the end of 30 days, the parent vials are extracted with the appropriate solvent, and the extracts examined by the applicable method for the presence of the original target compound and any anticipated transformation products. Identification of dead end transformation products, those which accumulate without further change, reveals the next step in the process— isolating cultures, using the concepts described earlier, to collect organisms capable of the transformation of the dead end product. In this fashion, blocks to mineralization are identified and removed. Again, referring specifically to PCBs, FIG. 1 shows a pathway for their aerobic biodegradation. Dead end, or accumulating metabolites in this pathway include, for example, chlorobenzoates, chlorinated alkanes, catechols, gentisate and protocatchuate.

The steps described above yield a collection of organisms capable of executing the various processes necessary to reduce the offending compound, either to $CO_2$, or other easily degraded components. As it is difficult, at best, to introduce a simple organism into an unfamiliar ecosystem with the expectation that it will establish itself in the midst of the native population, the probability of introducing multiple cultures successfully is minimal. Thus, it would be an advantage to introduce the entire mineralizing consortium at one time. The blending of the various biotypes which comprise the consortium is facilitated to some degree by the fact that: (1) "downstream" biotypes metabolize the products produced by "upstream" biotypes; and (2) the various biotypes which comprise the consortium will have been isolated under essentially identical conditions. This blending is effected, for example, through the introduction of subsequently added cultures in graded ratios. For example, in the presence of the original target compound and first "dead end" metabolite at $\frac{1}{10}$ the target's concentration, the first two groups are introduced in a graded series 1:1, 1:2, etc., through 1:10 with ratio reversing in favor of the group held constant in the first series. Combined cultures are screened for the desired activity, in this case the production of the third road block metabolite, and the process continued.

In use, the consortium of specific degraders may be applied to contaminated matrices such as soils sediments and water. The application of the consortium to the contaminated matrices may be in any of the variety of conventional methods applicable to the particular matrix. For example, soils or sediments can be excavated, slurried and treated in treatment tanks, natural ponds of lagoons or man-made ponds which are suitable for the introduction of the consortium.

In a preferred embodiment, a lined bioremediation site of suitable size is constructed. The lining of the site comprises an impermeable barrier to control leeching through the soil column and runoff from the site. A piping manifold is then designed and installed within the lined bioremediation site. Excavated soils or sediments are then spread within the lined bioremediation site. Preferably, the contaminated soils are spread to a depth of no more than about 18 inches. However, alternative configurations such as piling or bunkering with a removable manifold to ease cleaning and loading may facilitate vertical distribution and aeration of the contaminated matrix.

The manifold is then used to charge the contaminated soils or sediments with a nutrient solution containing a complete mineral salts mixture and dextrose (or other suitable carbon source) to prime the matrix and facilitate the utilization and depletion of available carbon source. This charge is followed by the delivery of air ($O_2$, $N_2$, $CO_2$) at low pressure as is typical of bioventing processes. This procedure is repeated as many times as is necessary until tests measure either a decline in the magnitude of carbon dioxide and/or a decrease in the recoverable microbial population. This process depletes the native population and soil of competing carbon sources, leaving the PCBs as the primary carbon source available from which microbes may derive their energy.

The consortium of specific degraders is then added to via the manifold to the prepared matrix. Preferably the consortium is added until the matrix contains approximately 25–30% of the desired consortium per gram of soil. Air is then added via the manifold to complete saturation of the site. The bioremediation site is then monitored for levels of contaminant, intermediates, pH, trace elements and cometabolites, as necessary. As toxic compounds are degraded, levels of various cometabolites increase. Periodically, it may be necessary to amend the soils or sediments with supplemental nutrients, microbial consortiums or adjust the pH as necessary to support the bioremediation process.

The bioremediation site may also be overseeded with a non-flowering intrusive ground cover whose roots carry the degrading consortium of microbes. The plants will serve as an invasive alternative delivery system for the microbial consortium, and aid in controlling runoff and air emissions.

EXEMPLIFICATION

This example relates to the reductive dechlorination of Araclor 1254 and 1260. These toxic compositions comprise a mixture of polychlorinated biphenyls comprised mainly of hexa- and heptachlorobiphenyls which have previously been determined to be difficult substrates for microbial attack.

Methods i) Selection of Soils

PCB contaminated soils were obtained from two sites in Brattleboro and Newport, Vermont. Chlorobenzoate utilizing cultures were collected from soils obtained from the first 2 cm of soil in a poplar bog at Hinesburg, Vt., a source of complex resins.

ii) Primary Enrichment

Coverslip cultures were prepared as described utilizing either Araclor 1254 or 1260 in methanol, or simply methanol as a control. Secondary degraders were collected utilizing coverslips overcoated with 4-chlorobenzoate.

iii) Secondary Enrichment

Forty mL vials were prepared through the addition of 5 mg of Araclor 1254 or 1260 in methanol or methanol only. Sets were withdrawn from the primary enrichment and placed into the secondary vials with their attached biofilms. These vials were allowed to incubate for five days, after which they were vigorously shaken and 0.2 mL transferred to fresh vials containing either a mixture of 0.05 mg each of Araclor 1254 or 1260 or the Araclor mixture plus 0.1 mg of catechol. This set was allowed to incubate for 10 days, at which time they were combined and the dual culture used to incubate a series designed to examine the effects of MeOH and bromocresol purple on the degradation of the Araclors.

iv) Cultures

Cultures were established in 100 mL serum bottles containing the basil medium, inoculum, amendments and 1.25 mg each of Aroclors 1260 and 1254. Cultures were routinely incubated for two weeks and six to eight weeks at room temperature, 25–28° C.

v) Extraction

Cultures were extracted by shaking with 40 mLs of chloroform allowing the mixture to separate and drawing off the solvent layer. This procedure was repeated with hexane. Extracts were concentrated to a final volume of 2.0 mLs.

vi) Paper Chromatography

One hundred ul of each extract, containing a possible maximum of 0.125 mg of PCB were spotted onto 0.25×6 inch strips of Whatman P81 Cellulose phosphate ion exchange chromatography paper. Standards containing total weights of 100, 10, 1, 0.1, 0.01, 0.001 ug 4-chlorobenzoate and catechol were similarly spotted. All chromatograms were developed against a hexane: acetic acid: methanol (5:4:1) mixture.

Results i) Effect of Methanol and Bromocresol Purple on PCB Degradation

A total of thirty vials were prepared through the addition or deletion of methanol, bromocresol purple, and Aroclor according to the following matrix:

|    | A+, M+, B+ | A+, M−, B+ | A+, M+, B− | A+, M−, B− | A−, M+, B+ |
|----|------------|------------|------------|------------|------------|
| I  | 1, 2       | 7, 8       | 13, 14     | 19, 20     | 25, 26     |
| IK | 3, 4       | 9, 10      | 15, 16     | 21, 22     | 27, 28     |
| UI | 5, 6       | 11, 12     | 17, 18     | 23, 24     | 29, 30     |

A = Araclor
M = Methanol
B = Bromocresol Purple
I = Inoculated
IK = Inoculated
UI = Uninoculated Araclors 1254 and 1260 were added as a methanol solution to presterilized 40 mL VOAs, and the vials placed at a slight angle in a dry sand bath at approximately 121° C. Upon evaporation of the methanol, a mixed Araclor film with a weight of 0.5 mg was deposited on the vial.

Two mL of GC grade methanol was aseptically added to the appropriate vials as was 5 mL of sterile 1% bromocresol purple solution. All vials were capped and held at 30° C. for two days to assess their sterility. At the end of this period, each inoculated vial received 0.2 mL of the combined culture and inoculated killed received 0.2 mL of an autoclaved aliquot of the combined culture. Otherwise identical control cultures were uninoculated. All vials were placed at 30° C. A set of control cultures were established whereby 0.2 mL of either live or killed culture was added to 10 mL of mineral salts broth and immediately extracted with 20 mL of chloroform. This set was utilized to detect any extractables which were associated strictly with the inoculum as opposed to microbial transformation of the target compounds.

ii) Thin layer Chromatography

After ten days of incubation, all odd numbered vials were removed from incubation and extracted, twice with 5 mL of chloroform per extraction; the extracts were combined and concentrated to 1 mL. Two mL autosampler vials with Teflon lined caps were used to store the extracts at −10° C. for further analysis.

At fifteen days, the remaining even numbered cultures were removed and recharged with 10 mL of mineral salts and methanol or bromocresol purple as appropriate. On day forty-five, the remaining vials were extracted with chloroform, concentrated and stored in autosampler vials as noted previously.

Extracts were spotted, 50 uL/lane, on silica gel coated glass backed plates etched with 0.25 inch lanes. Plates were developed for 1.5 hours in hexane, methanol, and acetic acid 8:1:1. This particular solvent system facilitated the separation of all components of the standard, with the exception of the Aroclor species which eluted as a single band.

Based upon the results of these trials (see following section), enrichment cultures were established to obtain a population which could mediate the mineralization of 4-chlorobenzoic acid. These cultures were sought in woodland soils among species with high resin content, such as hemlock, poplar, etc. Cultures were established initially by the same coverslip method described earlier, with the exception of the addition of 20 mg/L of glucose to the soil slurry to "prime" the cultures and help in the depletion of endogenous carbon.

Upon the detection of apparently irreversible acidification of cultures enriched for chlorobenzoate utilization a first attempt was made to combine those organisms which had been determined to initiate the transformation of PCB with those which attack the dead end product, chlorobenzoate. This was accomplished by adding 0.1 mL of each culture to vials containing 0.5 mg of Aroclor 1254, 2 uL of methanol, 5 uL of 1% bromocresol purple. The combined cultures were maintained with daily agitation and venting for seven days, by which time the culture displayed heavy growth, had acidified, and effervesced when shaken indicating the generation of $CO_2$ or some other volatile product. After cloning by passage to fresh vials, the combined culture was extracted as described previously and examined for the byproducts of PCB metabolism by thin layer chromatography.

In nature, the ability of microbial populations to mineralize PCB appears to be self-limiting for a number of reasons. These include, for example, common place effects such as a decline in pH due to generation of HCl from dechlorination of the biphenyl ring and utilization of available $O_2$ to more exotic, less easily controlled aspects of the process, such as production of chlorocatechols and/or chlorobenzoates. Although organisms capable of the utilization of both of these classes of compounds have been discovered in nature, they have not been reported to occur in conjunction with PCB degrading forms, which allowed the assembly of a group of microbes which utilized Araclors and catechols as sole carbon sources. These cultures were established under identical nutritional, atmospheric and temperature conditions, with carbon sources as the sole variable. This approach yielded collections of organisms which could coexist, yet not directly compete for carbon. Thin layer chromatography (TLC) was utilized to compare possible transformation products with standards, and also to compare cultures to each other.

The first TLC series examined the effect of Araclor 1254/1260 in combination with methanol, bromocresol purple on the transformation of PCBs, and was divided into two segments—one set extracted after ten days, the second after forty-five days. Of the fifteen combinations of Araclor, bromocresol purple, methanol and inoculum originally assembled, only three demonstrated any appreciable activity, while the uninoculated and inoculated killed vials were used to establish which bands could be attributed to the base medium, cell debris, and solvent impurities. These three had one component in common, bromocresol purple. The two permutations which contained Araclor, but no bromocresol purple, did not contain bands other than those which may be attributed to either the PCB or the medium. This indicates that the presence of methanol and PCB alone is inadequate to promote the short term breakdown of Araclor 1254 and 1260. Culture 4/15-25 contained only MeOH and bromocresol purple (BCP). This resulted in a longwave UV blue fluorescent spot at a point lagging slightly behind the 4-chlorobenzoate standard. This band appears in both the 10 day and the 45 day cultures unmoved in relation to the chlorobenzoate standard band. It apparently represents a dead end product from the degradation of BCP.

Culture 4/15-7 and 8, containing only Araclor and BCP, produced a single band which appeared after spraying the plate with an acrylic preservative. This short-wave fluorescent blue band appears to be a transformation product of either the Araclor, bromocresol purple, or both.

Culture 4/15-1 was definitely the most lively, with five non-PCB, non-medium related bands. Of these five, two may be identified as the methanol band and the bromocresol purple Araclor Band. The other three appear to be unique to this culture, with the band demonstrating the greatest Rf being identified with the 4-CBA standard. In the sister culture 4/15-2, all bands except that of Rf equal to the CBA disappear, again indicating that it is a dead end product, most likely a chlorobenzoate of either low or single chlorine number. No bands which could be identified as catechol were seen in any of the cultures. It appears that the transformation carried out by this particular group of microorganisms dead ends at the benzoate step.

This realization necessitated, as anticipated, a search the next organism in the chain, in this case the organism or group capable of the utilization of chlorobenzoate. A different approach was utilized for this group, deliberately seeking out soil which would naturally contain a high concentration of aromatic substances (poplar) and depleting it background carbon by the addition of 40 ppm of dextrose to the soil slurry. Coverslip cultures were planted as with PCB containing soils, but the slips were coated with 4-CBA or PCB. Coverslips were removed at 7 and 14 days and placed in vials containing 10 mL mineral salts agar and 0.5 mg 4-CBA. These, in turn, were allowed to incubate at room temperature for 30 days. At the end of this time, one culture which demonstrated stable acidification in the absence of methanol and bromocresol purple was blended 1:1 with the most active Araclor degrading culture from the previous experiment, 4/15-1A, with 1254 and MeOH. This new culture was placed at 30° C. and examined daily for any significant change. This combination resulted in a culture which rapidly and irreversibly acidified and liberated large amounts of gas, presumably $CO_2$. TLC of this culture resulted in a single band of Rf identical with that of the 4-CBA standard. The implication of this is that the PCB was transformed to CBA, which in turn accumulated before it was further degraded to $CO_2$. Older cultures yielded similar results, with PCB brands of greatly diminished intensity and the CBA band missing entirely. It is believed that the cultures ultimately degrade the CBA generated during the transformation of at least some proportion of the Araclor to $CO_2$.

iii) Soil Amendment

Methods were further enhanced through the addition of inducers for the methane and ammonia monoxygenase systems, and also through the addition of terepenes, known to act as cometabolites and to enhance the biodegradation of PCBs. The terepenes were derived from extracts of plant materials, more specifically from hot alcohol extraction of dill weed, spruce and pine needles. Addition of B-complex vitamins was found to further accelerate the process. The methylotrophic yeast, Pichia, was examined as both a source of cofactors and monoxygenase activity. Terepenes were added over time to concentrations of 10-fold the concentration of PCB's. Methane monoxygenase inducers were added to concentrations of 50 ppb, and B vitamins were added to concentrations of 40 pph.

Thin layer chromatography of extracts of cultures incubated with the soil amendments indicated at least 90% removal of the mixture of Aroclors 1254 and 1260. Upon exposure to short-wave UV, all PCB standards yielded a single band at an Rf of 1.0. 4-chlorobenzoate appeared at an Rf of 0.73 and catechol was unmoved from the point of origin. At two weeks all standards were UV dark and clearly visible. By contrast, the PCB and catechol bands were missing entirely from the PCB containing cultures. A wide, poorly resolved band in the proximity of the 4-chlorobenzoate was clearly visible. At 6 to 8 weeks the standard remained the same, the PCB and catechol bands were still absent, and the 4-chlorobenzoate band had also disappeared. The poorly resolved bands at Rf 0.85–0.65N, present at two weeks, were probably indicative of mixed chlorobenzoates resulting from the transformation of multiple cogeners.

Efficiency of degradation was estimated from the thin layer chromatography results. At a minimal extraction efficiency of 1%, (since the extraction of PCBs in hexane is a standard EPA method, it is believed that the extraction's efficiency to be considerably greater than 1%) 1.25 ug of PCB would have been spotted, an amount which was determined to be detectable from the standard preparations. The lack of discernible PCB bands from culture extracts, coupled with the ability to visualize 0.001 ug of PCB, indicates transformation of greater than 90% of the original mixture of PCBs. Similarly, the lack of an identifiable catechol band after two weeks, and the transformation of the chlorobenzoates after two weeks and its disappearance after 6 to 8 weeks, also indicate the transformation of those respective compounds.

I claim:

1. A method for assembling a consortium of specific degraders of a xenobiotic compound of interest, comprising:
   a) providing a first population of microorganisms isolated from a first source containing the xenobiotic compound of interest, or structural homologs thereof;
   b) incubating the first population of microorganisms under conditions appropriate for growth with media containing the xenobiotic compound of interest as a carbon source;
   c) screening for the ability of the population to initiate degradation of the xenobiotic compound of interest;
   d) identifying an accumulating intermediate in the degradation pathway of the xenobiotic compound of interest;
   e) providing a second population of microorganisms isolated from a source containing the accumulating intermediate in the xenobiotic degradation pathway identified in step d), or structural homologs thereof;
   f) incubating the second population of microorganisms under conditions appropriate for growth with media containing the accumulating intermediate as a carbon source;
   g) screening for the ability of the second population of microorganisms to degrade the accumulating intermediate;
   h) optionally repeating steps d)–g) to identify additional accumulating intermediates and populations of microorganisms which specifically degrade such additional accumulating intermediates; and
   i) combining the populations of microorganisms identified in the preceding steps as participants in the pathway of degradation of the xenobiotic compound of interest under conditions appropriate for the integration of the populations into a single consortium of specific degraders of the xenobiotic compound of interest.

2. The method of claim 1 wherein the xenobiotic compound of interested is a polychlorinated biphenyl.

3. The method of claim 2 wherein the screening of step c) comprises monitoring pH levels.

4. The method of claim 1 wherein the screening of step c) comprises monitoring breakdown product levels.

5. The method of claim 1 wherein the combination of populations of microorganisms referred to in step i) is achieved through addition in graded ratios.

6. The method of claim 2 wherein the accumulating intermediates of step d) are selected from the group consisting of chlorobenzoates, chlorocatechols, gentisate and protocatchuate.

7. A method for degrading a xenobiotic compound of interest in a contaminated matrix, comprising:
   a) providing a consortium of specific degraders of the xenobiotic compound of interest, produced by the method comprising:
      i) providing a first population of microorganisms isolated from a first source containing the xenobiotic compound of interest;
      ii) incubating the first population of microorganisms under conditions appropriate for growth with media containing the xenobiotic compound of interest as a carbon source;
      iii) screening for the ability of the population to initiate degradation of the xenobiotic compound of interest;
      iv) identifying an accumulating intermediate in the degradation pathway of the xenobiotic compound of interest;
      iv) providing a second population of microorganisms isolated from a source containing the accumulating intermediate in the xenobiotic degradation pathway identified in step d), or structural homologs thereof;
      vi) incubating the second population of microorganisms under conditions appropriate for growth with media containing the accumulating intermediate as a carbon source;
      vii) screening for the ability of the second population of microorganisms to degrade the accumulating intermediate;
      viii) optionally repeating steps d)–g) to identify additional accumulating intermediates and populations of microorganisms which specifically degrade such additional accumulating intermediates; and ix) combining the populations of microorganisms identified in the preceding steps as participants in the pathway of degradation of the xenobiotic compound of interest under conditions appropriate for the integration of the populations into a single consortium of specific degraders of the xenobiotic compound of interest; and b) contacting the consortium of specific degraders of step a) with the contaminated matrix containing the xenobiotic compound of interest under conditions appropriate for degradation of the xenobiotic compound of interest.

8. The method of claim 7 wherein the contaminated matrix is selected from the group consisting of soils, sediments and water.

9. The method of claim 8 wherein the xenobiotic compound of interest is a polychlorinated biphenyl.

10. The method of claim 9 wherein the screening of step c) comprises monitoring pH levels.

11. The method of claim 7 wherein the screening of step iii) comprises monitoring breakdown product levels.

12. The method of claim 7 wherein the combination of populations of microorganisms referred to in step i) is achieved through addition in graded ratios.

13. The method of claim 9 wherein the accumulating intermediates of step iv) are selected from the group consisting of chlorobenzoates, chlorocatechols, gentisate and protocatchuate.

* * * * *